(12) United States Patent
Markham

(10) Patent No.: US 8,114,076 B2
(45) Date of Patent: Feb. 14, 2012

(54) INSTRUMENT FOR ENDOSCOPIC SURGERY

(76) Inventor: Harold A. Markham, Beverly Hills, CA (US)

( * ) Notice: Subject to any disclaimer, the term of this patent is extended or adjusted under 35 U.S.C. 154(b) by 1189 days.

(21) Appl. No.: 11/895,160

(22) Filed: Aug. 23, 2007

(65) Prior Publication Data

US 2009/0054732 A1 Feb. 26, 2009

(51) Int. Cl.
*A61B 18/12* (2006.01)
(52) U.S. Cl. .............. 606/52; 606/51; 606/207
(58) Field of Classification Search ............. 606/51, 606/52, 205–207
See application file for complete search history.

(56) References Cited

U.S. PATENT DOCUMENTS

| | | | | |
|---|---|---|---|---|
| 5,176,699 A | * | 1/1993 | Markham | 606/206 |
| 5,217,460 A | * | 6/1993 | Knoepfler | 606/52 |
| 5,258,006 A | * | 11/1993 | Rydell et al. | 606/205 |
| 5,578,052 A | * | 11/1996 | Koros et al. | 606/174 |
| 5,964,779 A | * | 10/1999 | Mayenberger et al. | 606/205 |
| 2003/0018331 A1 | * | 1/2003 | Dycus et al. | 606/48 |
| 2003/0060816 A1 | * | 3/2003 | Iida | 606/29 |

* cited by examiner

*Primary Examiner* — Michael Peffley
*Assistant Examiner* — Daniel Fowler
(74) *Attorney, Agent, or Firm* — James M. Duncan, Esq.; R. Scott Kimsey, Esq.; Klein, DeNatale, et al.

(57) ABSTRACT

An instrument for endoscopic surgery includes a shaft having active and inactive portions, the active portion being reciprocable relative to the inactive portion. First and second operative elements are pivoted to the inactive portion of the shaft along substantially the same longitudinal plane. A handpiece includes an active and inactive branch hinged together, movement of the active and inactive branches of the handpiece together or apart shifting the active portion of the shaft relative to the inactive portion of the shaft.

11 Claims, 4 Drawing Sheets

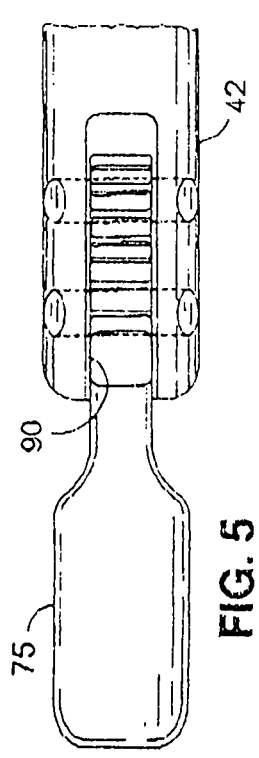
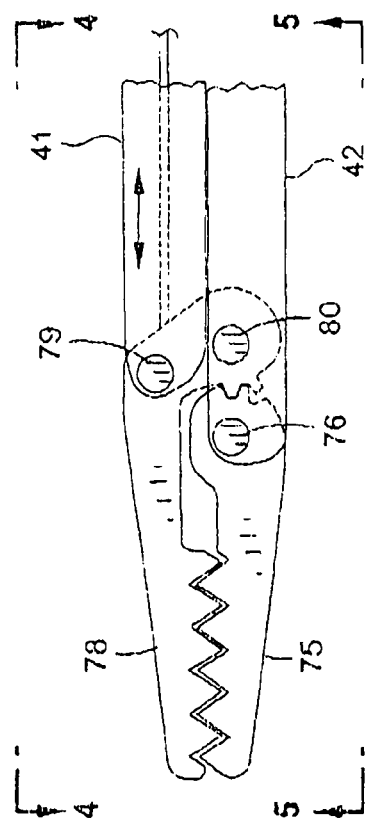
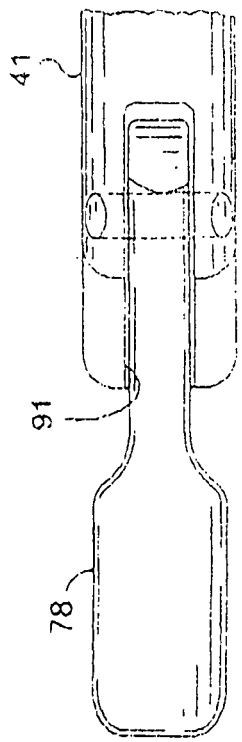
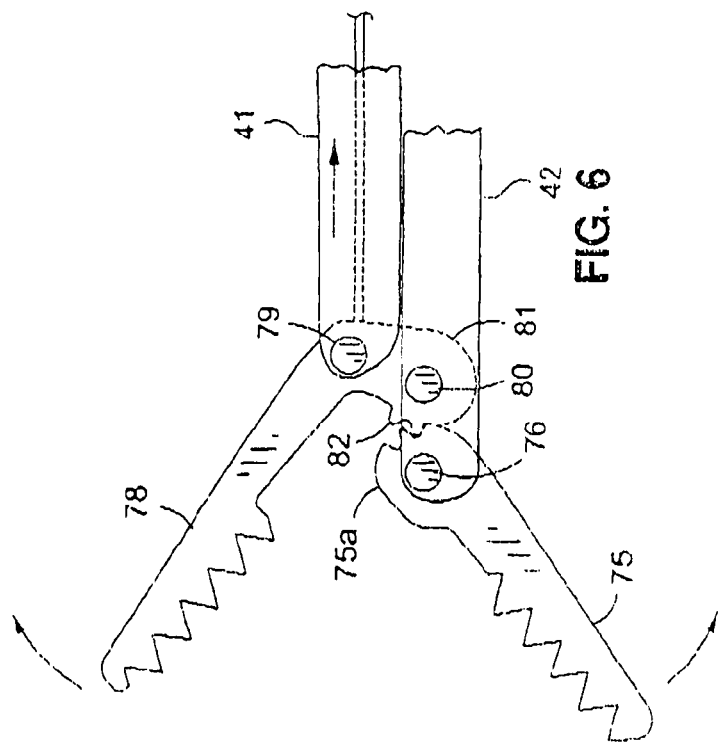

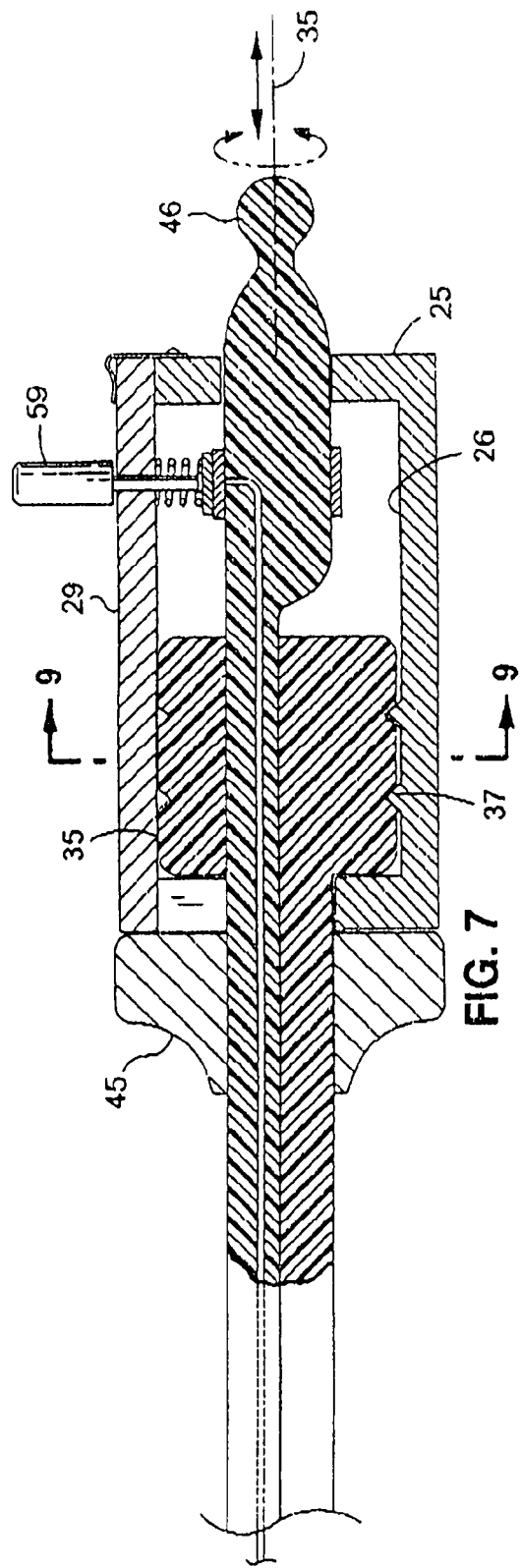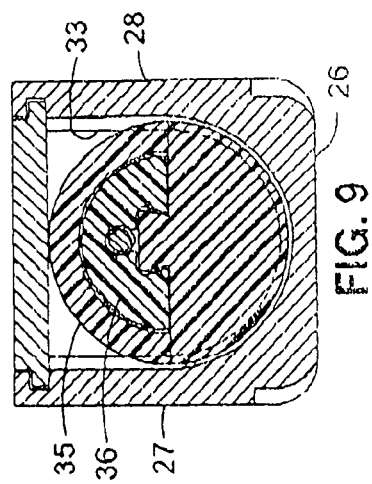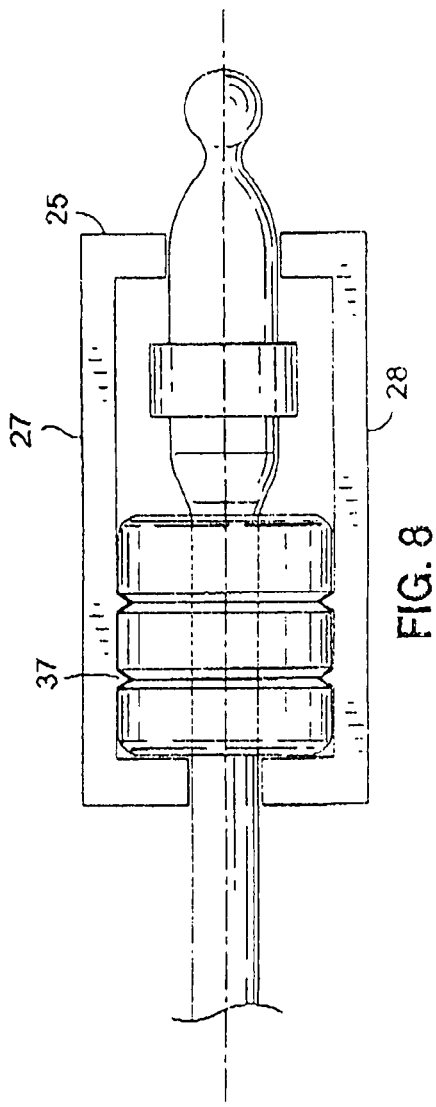

INSTRUMENT FOR ENDOSCOPIC SURGERY

FIELD OF THE INVENTION

An endoscopic surgical instrument economically suitable for one-time disposable use. Potential advantages are the ready substitution of different operative units during the same procedure, improvement of electrical insulation when used in electro-surgery, and improved active elements for operative units.

BACKGROUND OF THE INVENTION

This invention relates to endoscopic instruments of the class which includes a shaft whose distal end is inserted into a body cavity. At its distal end the instrument includes any one of a wide variety of active elements. At its proximal end there is a handpiece for actuation of the active element by the surgeon.

This type of instrument is well-known and is in widespread usage. The events at the site where the active elements accomplish their function are observed through a separate telescope system. Manipulation of the handpiece places the active element in an appropriate location and orientation and then actuates it to perform some surgical function. Such functions as occlusion, stapling, cutting and scission are commonplace.

Electro-surgical procedures are also enabled by such instruments. Cauterization is one such procedure, which frequently is used to staunch blood flow after a cutting procedure. Usually this electro-surgical sequence is done simultaneously with a cutting procedure. For example, scissor implements often form part of an electrical circuit that provides energy to coagulate and close a wound during the cutting phase.

A substantial industry has developed from these objectives. One example of a useful instrument is shown in applicant's U.S. Pat. No. 5,176,699, issued Jan. 5, 1993. This patent is representative of a large number of patents, all of which disclose and claim devices useful in endoscopy. It does not show the use of an instrument which is useful for electro-surgical procedures and which also is useful for procedures which do not use electrosurgery nor one which is especially suitable for one-time usage or for ready accommodation to a plurality of purposes.

Characteristic of these prior efforts is to provide at the active site a high frequency electrical current. This current is delivered at a high voltage through a long conductive member that extends through the instrument so as to be effective at the site, and not elsewhere. The problem is to get the electrical current to the exact place, and thereafter to diffuse it or otherwise conduct it to a ground such as the operating table without damage to other tissue, to the surgeon, or to the patient.

If all goes well, all of the current first goes only to the operation site, and from there it is harmlessly diffused.

The problem is that getting it only to the site is not a trifling matter. The extended metallic conductor from the handpiece to the active element is covered by insulation. Without the insulation, when this insulation would be the only protection, the patient or surgeon could be burned.

For insulation, these conductors are commonly coated with a layer of insulation that extends from the handset to the active element. This is a suitable arrangement if all goes well. However, the history of this instrumentation is replete with failures. Small "holidays" in the insulation caused by impact or by imperfect manufacture can and do permit substantial current leakage at weak or faulty places. Rubbing of the instrument against a rigid cannula through which it is passed and manipulated can also damage conventional insolation. The consequence, especially at the high frequencies employed, are internal burns in the patient, often to his serious damage.

Accordingly there exists a significant exposure to a risk that is avoidable only by perfection in the insulation. Perfection can be achieved, but in the practical world, one relies on statistical quality control and this leaves open the chance for failure in manufacture and in usage, although at a low rate. Still, a patient with a burn is not comforted by a low degree of risk.

It is an object of this invention to provide instrumentation that greatly reduces this kind of damage and risk.

Another disadvantage of known instrumentation of this type, not necessarily applicable only to electrosurgery, is the widespread use of the surgeon's thumb as the driver of the handpiece to actuate the active element. This is fatiguing and can lead to carpal tunnel problems for the surgeon. This invention eliminates this problem Even further, conventional instrumentation does not provide for the quick and economically-justifiable substitution of one shaft and active element for another to an individual handpiece during a procedure. If such were made available to him, it would be a significant advantage to the surgeon and a major economic advantage, especially when provided as disposable one-time-use active elements. In contrast many instruments with disposable active elements include them as a unit with the handpiece, all of which is discarded after use.

The instrument of this invention enables the use of only one handpiece (which can readily be sterilized), and the ready removal and replacement of the shaft with another shaft each with a different active element during a procedure requiring only a momentary interruption and involving least distraction to the surgeon who does not have to remove his hand from the handpiece. As a consequence, there results a system in which a single handpiece can accommodate a sequence of single-use shafts and active elements, which themselves are reasonably affordable, and which improve the surgeon's access to different active elements during a procedure.

An expensive handpiece to be reused needs sterilization before each succeeding procedure, and this can often be economically justified. Alternatively, when a single use (single procedure) handpiece (usually plastic) is used and is to be discarded, still only one handpiece need be provided for the entire operation, and it can economically be discarded. With this invention, either way the instrument enables important savings.

This invention provides a surgical instrument system useful with or without electrosurgery provisions, and has an ergodynamically suitable handpiece that readily accommodates removable and replaceable shafts carrying respective active elements of various kinds. The variety of available active elements enables this system to function for nearly all endoscopic procedures.

Additionally, this invention enables the use of electrical conduitry that, while it may be coated with insulation, has the further advantage of being further isolated in insulation material of which the shaft is made.

BRIEF DESCRIPTION OF THE INVENTION

An endoscopic instrument according to this invention includes a handpiece for the surgeon to hold and with it to manipulate the instrument. The handpiece includes an active and an inactive branch which are hinged together. The active branch is forward of the inactive branch. The inactive branch is engaged by the thumb, while the active branch is engaged by the fingers for actuation. This contrasts with conventional handpieces in which the thumb is used for actuation.

A shaft includes an active and an inactive portion. The inactive branch carries or is receptive to a mount. The mount receives and holds the inactive portion of the shaft. The active branch of the handpiece carries a socket that engages the active portion of the shaft. Accordingly, scissor-like movement of the handpiece will reciprocally shift the active portion of the shaft relative to its inactive portion. The inactive portion of the shaft remains stationary along with the inactive branch of the handset to which it is connected.

According to a preferred but optional feature of this invention, the active and inactive portions of the shaft are slidably coupled together, One of the shaft portions includes a longitudinal re-entrant slot, and the other includes an engaging re-entrant key. The shaft itself is made of insulation material so as to shield the patient from leakage current from a conductor carried by the active portion of the shaft. The conductor itself is isolated by the two shaft portions.

The active element at the distal end of the shaft includes two operative parts. In cutting operations these operative parts might for example be scissor blades. In a gripping operation they might be jaws. These are operatively coupled to each other and pivoted to respective shaft portions such that reciprocation of the active portion of the shaft relative to the inactive portion results in opening and closing movement of the parts as directed by the surgeon. It is also possible to provide a single blade pivoted to one of the shaft portions for making a single cut. For electrosurgery the conductor will be connected to one or both of the operative parts.

The shaft is rotatably secured in the mount so that it can be rotated to suit the surgeon's requirements.

The above and other features of this invention will be fully understood from the following detailed description and the accompanying drawings, in which:

BRIEF DESCRIPTION OF THE DRAWINGS

FIG. 3 is an enlarged fragmentary side of active element of region 3 in FIG. 1;

FIG. 4 is a top view of FIG. 3 taken at line 4-4 therein;

FIG. 5 is a bottom view of FIG. 3 taken at line 5-5 therein;

FIG. 6 is a fragmentary side view of the operative elements of FIG. 1 with the jaws open;

FIG. 7 is a fragmentary cross-section taken at line 7-7 in FIG. 1;

FIG. 8 is a fragmentary top view of a portion of FIG. 1; and

FIG. 9 is a cross section taken at line 9-9 in FIG. 7.

DETAILED DESCRIPTION OF THE INVENTION

Figures 1, 2:
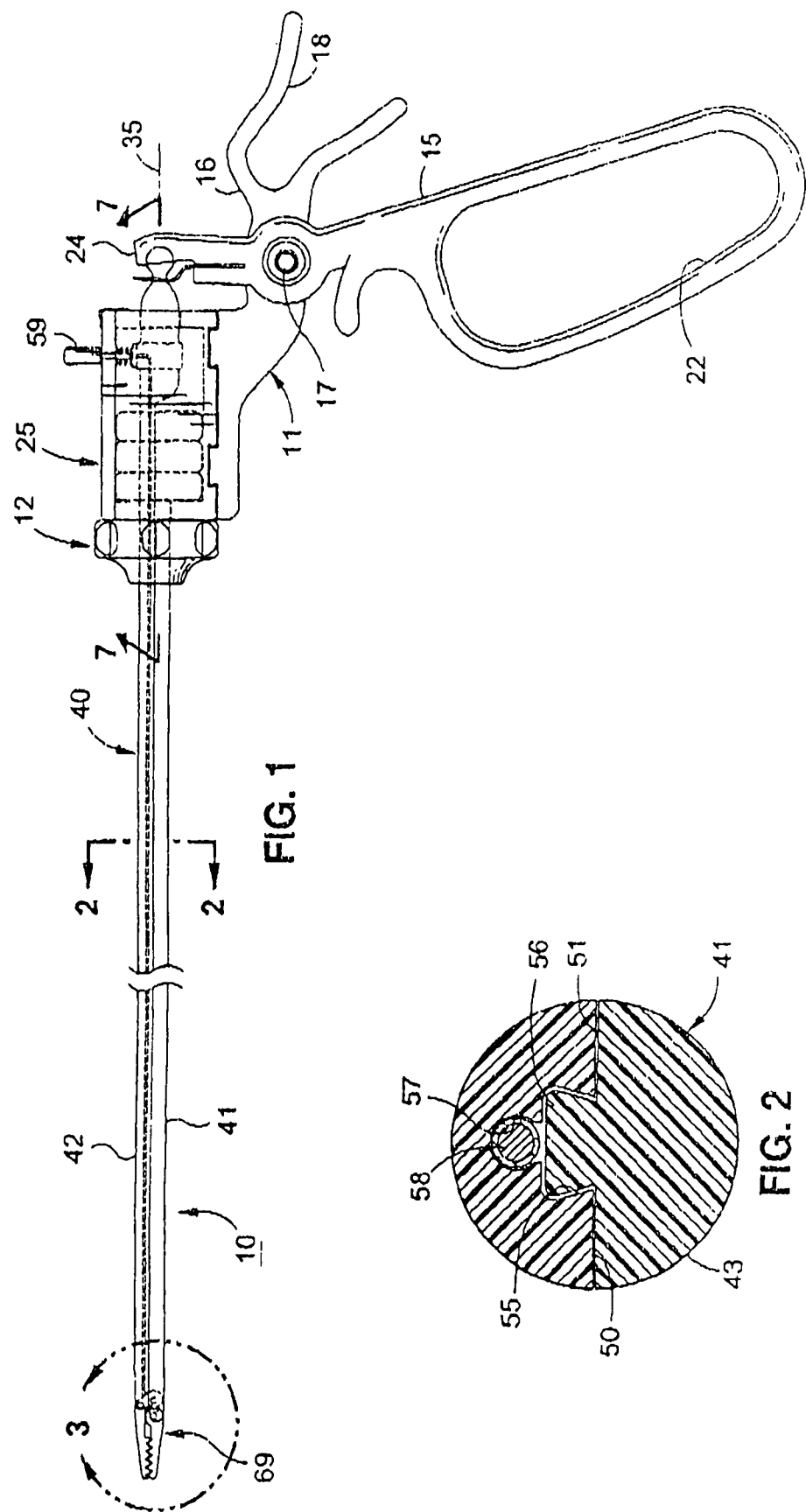
FIG. 1 is a side view of the presently preferred embodiment of the invention.
FIG. 2 is a cross-section taken at line 2-2 in FIG. 1.
Figure 1A:
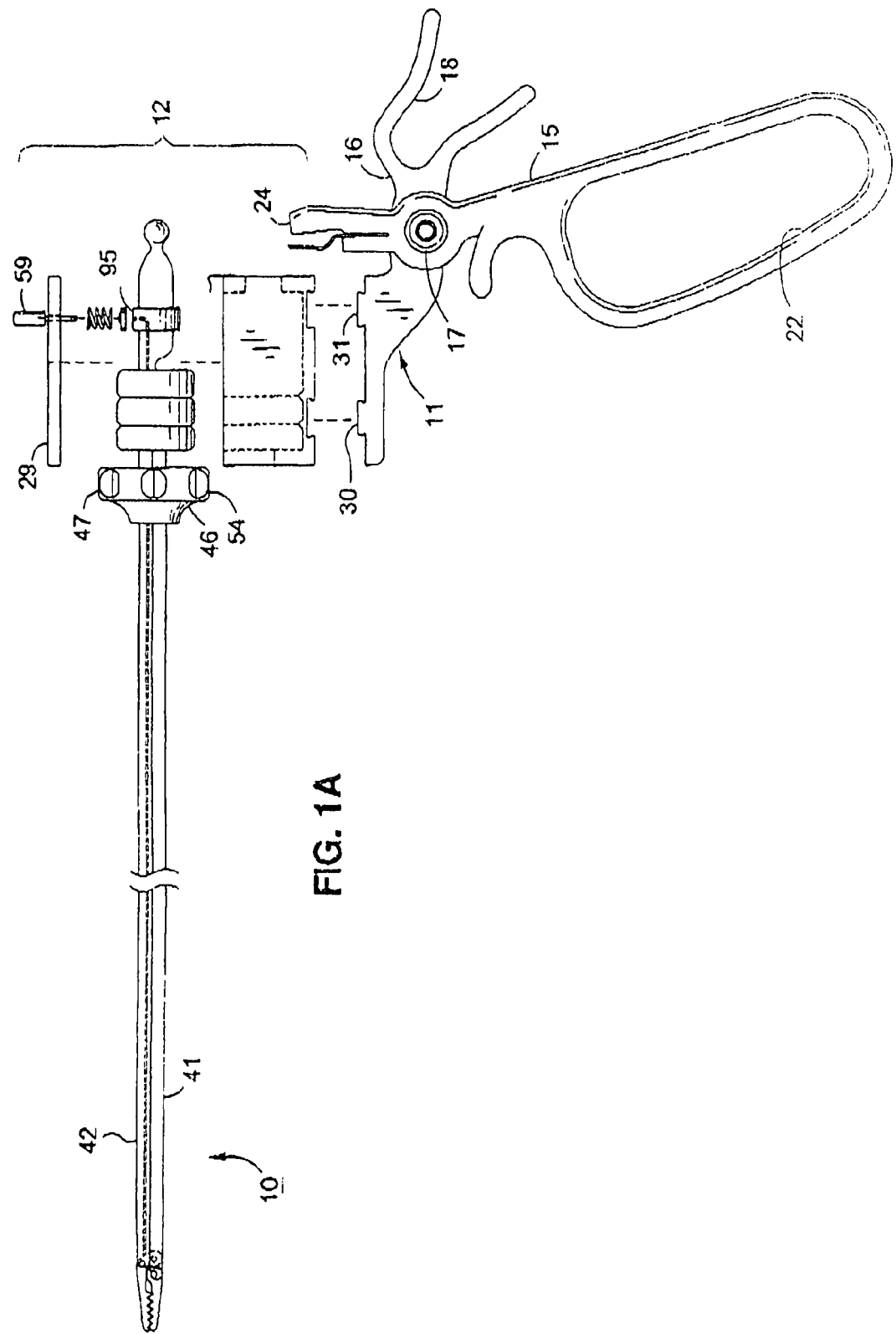
FIG. 1A is an exploded view of FIG. 1.

A complete endoscopic instrument 10 according to this invention is shown in FIG. 1. It is basically made in two separate parts: a handpiece 11 and an operative unit 12. They are separably joined together so that unit 12 can be removed and replaced either after a procedure and before the next one, or during a procedure. When a different set of operating elements is desired, a quick change of the operative unit is available. The handpiece can be kept in the surgeon's grip while the change is made, or later separated from the operative unit and sterilized if it is to be reused. In practice the operative unit is intended to be used only for one procedure and then discarded, while the handpiece, when made mostly of metal is much more expensive, is formed so as readily to be sterilized and later used again.

An advantage of this invention is that the handpiece can be made mostly of molded plastic parts and can be sterilized and used again. However, it is so inexpensive that instead it can economically be discarded, saving the costs of cleaning, sterilization and repackaging.

Whether it is made principally of metal or of molded plastic, handpiece 12 will be identically constructed. It includes an active branch 15 and an inactive branch 16. These branches are joined by a pivot 17. The inactive branch is the rear-most branch. It includes a cradle 18 or other suitable support device for the thumb, for example a loop. Cradle 18 may be integral with the remainder of the inactive branch. If preferred, a swivel joint may be provided to connect it to the remainder of the inactive branch to allow the surgeon's thumb to assume its most comfortable position Active branch 15 includes a finger loop 22. Cradle 18 and finger loop 22 are on the same side of the pivot so as to enable a scissor-like operation when they are brought together or moved apart.

Active branch 15 has on its end across the pivot from the finger loop a socket 24 for a purpose yet to be described.

As will now be seen, when the handpiece branches are moved moved toward and away from one another, socket 24 will move in an arc with a component of motion along longitudinal axis 35 of the instrument.

This is the basic handpiece. It will be observed that motion of socket 24 (and what it moves) is caused by finger motion. The thumb of the hand is still. Surgeon fatigue is greatly reduced.

Operative unit 12 includes an elongated shaft 40. Shaft 40 comprises two axially-oriented portions: inactive portion 41 and active portion 42 which are held together against separation, but so as to provide for relative reciprocal movement.

The shaft has an external cylindrical shape provided by its two portions (FIG. 2). Inactive portion 41 has a semi-cylindrical base 43 forming part of the outer wall of the shaft. As will later be shown it is structurally connected to the inactive branch of the handpiece by a mount. Its engagement to the mount stabilizes the operative unit on the handpiece and thereby to the inactive portion branch of the handpiece.

The operative unit is rotatable around the longitudinal axis. Its portions are relatively shifted when the surgeon moves the branches of the handpiece relative to one another.

For rotation of the shaft, a ring 45 is based on the inactive portion. By turning this ring the operative unit can be rotated. The ring is conveniently made in two pieces. Piece 46 is formed as an integral part of the inactive portion 41 of the shaft. A separate semi-circular piece 47 is removably attached only to the inactive portion to complete the ring. While it will rotate the entire shaft, including the active portion, it permits independent axial movement of the active portion. For example it may be connected to piece 46 by an axial tongue and groove assembly (not shown).

Shaft portions 41 and 42 are preferably externally semi-circular in cross-section (see FIG. 2). They closely abut one another, slidably, along flat surfaces 50 and 51. Surface 50 is on active portion 42 and incorporates a longitudinally extending re-entrant groove 55. A re-entrant key 56 is formed on the inactive portion. This key may be formed of intermittent segments or may extend continuously as a single key for all or part of the length by the shaft. When the key is in the groove, the two elements are held against one another to prevent separation, and are axially reciprocally slidable relative to each other.

An axially-extending recess 57 is formed in the active portion, preferably inside groove 55, opening into it. While this recess could instead open directly onto surfaces 50 and 51, it is preferable to place it inside the groove where the insulating material of the shafts and key will provide additional isolation for a conductor 58 which is to be fitted into it.

A major potential advantage of this invention is the ready substitution of one operative unit for another during the course of a procedure. It is intended to be so simple that the surgeon can retain his grip on the handpiece while an assistant removes one unit and quickly replaces it with a different one. The surgeon need not lose his focus as he might if he had to let loose of one instrument and handpiece and then engage a new one.

The basis for this advantage is an intermediate mount 25 disposed between the handpiece and the operative unit. This mount can be provided in a number of ways, all of which are within the scope of this invention.

If desired, the inactive branch of the handpiece can be provided with retainers 30,31 that can releasably hold the mount to inactive portion 41 of the handpiece. Alternatively the retention features of the mount may be incorporated directly into the inactive branch of the handpiece.

In most practical assemblies an individual mount (which is inexpensive) will be made separately, and will be attached to the inactive shaft portion of each operative unit. In use, the substitution of one unit for another then will require only release of one mount from the handpiece and attachment of another. This is the quickest and least expensive substitution of operative units.

The mount preferably will be made as an independent part which can be attached either to the operative unit or to the handpiece, separable from both of them, or be provided as an integral part of either one.

Mount 25 includes a base 26, a pair of parallel spaced-apart side walls 27,28 and a closure 29. When installed, it is intended to engage the proximal end of the inactive shaft portion of the operative unit. When the mount is in place and an operative unit is on it, turning the ring will rotate the operative unit around axis 35 while permitting axial movement of the active portion.

The mount must, of course, be attached to the operative unit. This is conveniently done by placing its proximal end between side walls 27 and 28 and holding it there. To provide for axial retention and also to permit rotation of the operative unit as a whole body, a plurality of ribs 33 (FIG. 9) is formed on the walls. Closure 29 is removably detached to the base to retain the unit in the mount.

The retention is completed by fixing a half shell 35 (FIG. 9) to the inactive portion aligned with ribs 33. This shell includes a smooth passage 36 to clear the active portion for axial movement, but with outside grooves 37 axially aligned with similar groove 38 on the round half portion of the inactive portion. These parts represent a circular enlargement of the shaft at its proximal end. Closure 39 is releasably attached to the side walls to retain the proximal end. It is now reliably held to the handpiece.

Dimensions are selected so that ring 45 bears against the front face of the mount (FIG. 5). The operative unit is then firmly held in the mount, allowing for axial rotation of the operative unit as a whole, and enabling the actuation of the instrument by finger movement.

Ring 45 attends to rotation of the operative unit. Reciprocation is attained by means of attaching active portion 42 to socket 24. Obviously this must be connected only with the active portion, on the central axis 35 of the operative unit. For this purpose the inactive portion is "stepped down" to the axis where it provides a knob 46 that can conveniently be engaged.

In addition, it is necessary to provide a contact for the electrical conductor, as will now be described.

To provide for external connection while still protecting the surgeon, an external conductive band 58 is formed on the stepped down part of the active portion, connected to the conductor. This is provided inside the mount. A spring-loaded contactor 59 is placed in the mount adjacent to the band. It bears against it and provides a conductive terminal 60 for connection into an external circuit which will be shielded by the connector which connects the terminal to a source of current.

Surfaces 50 and 51 make a close engagement, and the conductor preferably fits inside the axial groove. When the elements 41 and 42 are made of non-conductive plastic, together they make an additional insulating enclosure for the conductor.

The conductor is a surprisingly thin wire. Preferably it is insulated by a coating of insulation which if perfect is sufficient. It carries no physical load when the handpiece is manipulated. It merely rides with the active portion, and is not exposed to external contact such as from other instrumentation.

Actuated elements 69 shown at the distal end of the instrument are double-jawed. These are two-piece devices one piece on each shaft portion which meet or cross on the central axis. Single piece elements, which for example might be a single blade either fixed or pivoted, may be used instead. The double-jawed arrangement best illustrates useful features of this invention.

Movement of the elements of the operative unit is caused by reciprocal movement of active portion 42 relative to inactive portion 41. This motion is caused by opening and closing the spacing between the handpiece branches. This shifts the shaft portion of the active element relative to the stationary shaft portion of the inactive element.

U.S. Pat. No. 5,176,699 shows a double jawed arrangement, of which this instant invention is an improvement. For convenience in disclosure, the example shown in the drawings is a clamp or grasper. Instead it could be a pair of scissor blades or parts of a stapler, for example. It includes a first member 75 pivotally mounted by hinge pin 76 to the active shaft portion 42. First member 75 includes gear teeth 75a centered around pin 76. A second member 78 is pivotally mounted to inactive shaft portion 41 by pivot pin 79.

A coordinating pivot pin 80 is spaced from and disposed on the inactive shaft portion 41 adjacent to pivot pin 79. A lever 81 is integral with second member 78 and extends to the coordinating pin. Lever 81 includes a set of coordinating gear teeth 82 centered on coordinating pin 80. Reciprocation of the active portion 42 will cause the first element to move angularly around pin 76. Lever 81 and gear teeth 82 rotate around pin 80. It is immaterial whether the members are mounted to the shaft portion as described. They could instead be mounted each to the other shaft portion.

Importantly, second member 78 gear teeth 75a and 82 mesh together. This is a functional linkage between the two members. They will open and close together, although their centers of rotation are spaced from one another. The dimensions of these instruments are quite small, so they open and close in near and accurate proximity. It is evident that while hinge pin 76 does not move exactly in a straight line, the axial movement is ordinarily less than about 5 mm so that any deviation from straight line movement is insignificant.

It should be observed that both of the jaw members are placed in U-shaped channels 90, 91 in their respective shaft element. Thus they are side-supported so as not to be deformed or deflected when the instrument is rotated and they are spaced apart, but still have clearances for their motions. Side-load stresses on the more delicate parts are greatly reduced or eliminated.

Comparison of this arrangement to that illustrated in U.S. Pat. No. 5,176,699 shows that the instant embodiment requires smaller overall dimensions. This is a significant advantage for operations in very close quarters. In the '699 patent each shaft element mounts a respective jaw member which contributes to the "height" of the installation, i.e. thickness at the location. In the instant device, the two active pivots are on the same shaft portion.

The arrangement thus far is useful with or without electrosurgery, The conductive element can be eliminated as often it will be when electro-surgery is not contemplated. If it is provided, it will be connected to the operative elements in known ways.

The instrument of this invention can be made almost entirely of moldable insulating hard plastic material. The operative devices will of course be made of metal, as will be whatever parts must be electrically conductive. Pivot pins will usually be made of metal. The resulting handpiece is economically disposable, as are the operative units. The operative units, which are relative inexpensive can be used disposably, with more costly handpieces.

Shafts made of molded or extruded plastic are an important but not essential cost reduction. In addition they provide back-up insulation for the conductor when electrosurgery is involved.

When electrosurgery is contemplated, a circuit must be established between conductor 53 and a source of current. For this purpose, peripheral conductive band 58 is formed around the rear extension of the active portion centered around the central axis 35 of the shaft and connected to the conductor. Contactor 59 is held in cover 29, and when the cover is in place it is pressed by spring 97 against the band. Terminal 60 formed as a banana plug is on circuit with the contactor and available for connection with external circuitry. The conductor, of course, extends to the working parts or parts of the instruments. If electrosurgery is not to be employed, terminal 60 may be left unconnected, or in the alternative, a plain cover without the circuit connector may be used.

This invention thereby provides important advantages to the patient including full utility at much less cost.

It also provides additional efficiency to the surgeon by reducing his fatigue and enables the quick and reliable substitution of one kind of operative unit for another while he holds the handpiece. No longer must he exchange entire instruments when a different need arises. He merely detaches one part and replaces it with another.

This invention is not to be limited by the embodiments shown in the drawings and described in the description, which are given by way of example and not of limitation, but only in accordance with the scope of the appended claims.

I claim:

1. An endoscopic surgical instrument comprising:
an operative unit which includes a shaft having a longitudinal axis, a proximal end; and a distal end, said shaft being adapted for its distal end to be inserted into a body and placed by the surgeon at a location in an orientation to perform a local procedure, said shaft comprising an active and an inactive portion, which extend together along said axis, the active portion being reciprocable relative to the inactive portion;
a first operative element pivoted to the inactive portion of the shaft and rotatably attached to the active portion of the shaft, the first operative element comprising coordinating gear teeth disposed on a surface thereof;
a second operative element pivoted to the inactive portion of the shaft, the second operative element comprising coordinating gear teeth disposed on a surface thereof, the coordinating gear teeth of the second operative element engaging the coordinating gear teeth of the first operative element such that the first and second operative elements open and close in response to the relative axial movement of the active and inactive shaft portions, and wherein the first operative element and the second operative element are pivoted to the inactive shaft portion along substantially the same longitudinal axis of the surgical instrument; and
a handpiece separably attachable to said operative unit, said handpiece comprising: an active and an inactive branch hinged together; means on said inactive branch for engagement with the inactive portion of said shaft, and means on said active branch for engagement with the active portion of the shaft, whereby movement of the active and inactive branches of the handpiece together or apart shifts the active portion of the shaft relative to the inactive portion of the shaft; the active branch of the handpiece being disposed forwardly of the inactive branch and engageable by the surgeons's fingers, and the inactive branch being engageable by the thumb; the shaft as a unit being rotatable relative to the handpiece, and the active portion being axially movable independently of the inactive portion.

2. A surgical instrument according to claim 1 in which said active and inactive shaft portions are made principally of molded of extruded plastic, said portions having substantially planar confronting surfaces and external rounded surfaces.

3. A surgical instrument according to claim 2 in which a re-entrant groove extends axially along one of its said confronting surface, and a re-entrant key projects from the other confronting surface, fitting in said groove and holding the shaft portions together for sliding movement relative to each other.

4. A surgical instrument according to claim 3 in which an axially extending recess in said active portion houses an electrical conductor.

5. A surgical instrument according to claim 4 in which said recess opens into said groove in said active portion.

6. A surgical instrument according to claim 2 in which a mount is attachable to said inactive branch of said handpiece to hold the proximal end of said operative unit.

7. A surgical instrument according to claim 6 in which said mount is initially attached to said inactive portion.

8. A surgical instrument according to claim 6 in which said mount is initially attached to said inactive branch of said handpiece.

9. A surgical instrument according to claim 6 in which said mount and said operative unit when joined together holds the inactive shaft portion against axial movement while permitting it to rotate, and allows said active portion to move axially while being rotatable with the inactive portion, said active portion extending beyond said mount to be engageable by the active branch of the handpiece.

10. A surgical instrument according to claim 6 in which said active portion extends beyond said mount to provide a connection to an electrical conductor.

11. A working operative unit for the distal end of an endoscopic surgical instrument, said operative unit including
a shaft having an axis, a proximal end, and a distal end, said shaft being adapted for its distal end to be inserted into a body and placed by the surgeon at a location and in an orientation to perform a local procedure, said shaft comprising an active portion and an inactive portion which extend together along said axis, the active portion being reciprocable relative to the inactive portion, said working operative unit comprising:

a first and a second operative element each pivoted to a different one of said active and inactive portions at said distal end, a first operative element including a gear pivoted to its respective shaft portion, a coordinating gear pivoted to the same shaft portion engaged to said gear on said first element and having an integral lever connected to said second operative element engaged to a gear rotatably mounted to said second operative portion so the elements open and close in response to relative axial movement of the shaft portions.

* * * * *